US011510594B2

(12) United States Patent
Kogure et al.

(10) Patent No.: US 11,510,594 B2
(45) Date of Patent: Nov. 29, 2022

(54) POSTURE DETERMINATION APPARATUS

(71) Applicant: PARAMOUNT BED CO., LTD., Tokyo (JP)

(72) Inventors: Takamasa Kogure, Tokyo (JP); Tomoko Inoue, Tokyo (JP); Toshihide Shiino, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 627 days.

(21) Appl. No.: 16/496,550

(22) PCT Filed: Dec. 5, 2018

(86) PCT No.: PCT/JP2018/044804
§ 371 (c)(1),
(2) Date: Sep. 23, 2019

(87) PCT Pub. No.: WO2019/111977
PCT Pub. Date: Jun. 13, 2019

(65) Prior Publication Data
US 2021/0106256 A1 Apr. 15, 2021

(30) Foreign Application Priority Data
Dec. 7, 2017 (JP) .............................. JP2017-235410

(51) Int. Cl.
*A61B 5/11* (2006.01)
*A61B 5/107* (2006.01)
*A61B 5/00* (2006.01)
*A61G 7/05* (2006.01)

(52) U.S. Cl.
CPC ............ *A61B 5/1116* (2013.01); *A61B 5/107* (2013.01); *A61B 5/4561* (2013.01); *A61G 7/05* (2013.01)

(58) Field of Classification Search
None
See application file for complete search history.

(56) References Cited

U.S. PATENT DOCUMENTS

| 6,874,181 | B1 * | 4/2005 | Connolly ............... A61G 7/001 |
| | | | 5/607 |
| 2007/0191742 | A1 | 8/2007 | Park |
| 2015/0164721 | A1 | 6/2015 | Miyashita et al. |

FOREIGN PATENT DOCUMENTS

| JP | 08-131421 | | 5/1996 |
| JP | 2001-095858 | | 4/2001 |
| JP | 2005-144042 | | 6/2005 |
| JP | 2005-253608 | | 9/2005 |
| JP | 2011-120667 | | 6/2011 |
| JP | 2012-152283 | | 8/2012 |
| JP | 2012152283 | A * | 8/2012 |

(Continued)

*Primary Examiner* — Adolf Dsouza
(74) *Attorney, Agent, or Firm* — Wenderoth, Lind & Ponack, L.L.P.

(57) ABSTRACT

A posture determination apparatus including at least two vibration sensors and a controller. The controller causes the vibration sensors to detect vibrations while the user is lying in bed, calculates waveforms from the detected vibrations and recognizes the characteristics of the waveforms, and determines the posture of the user based on the characteristics. Thereby, it is possible to provide a posture determination apparatus capable of appropriately determining the posture of the user which is one factor of the state of the user.

17 Claims, 16 Drawing Sheets

(56) References Cited

FOREIGN PATENT DOCUMENTS

| | | |
|---|---|---|
| JP | 2016-192998 | 11/2016 |
| WO | 2017/018506 | 2/2017 |

* cited by examiner

FIG. 7
PRONE POSITION
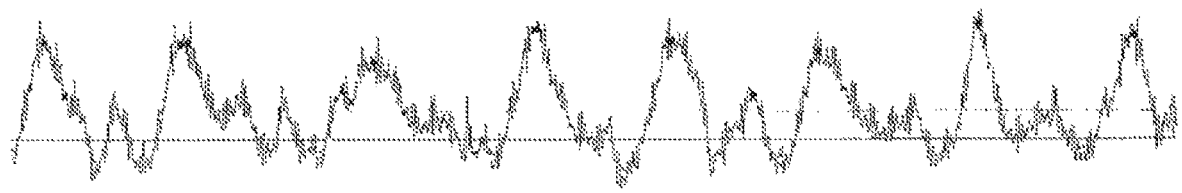
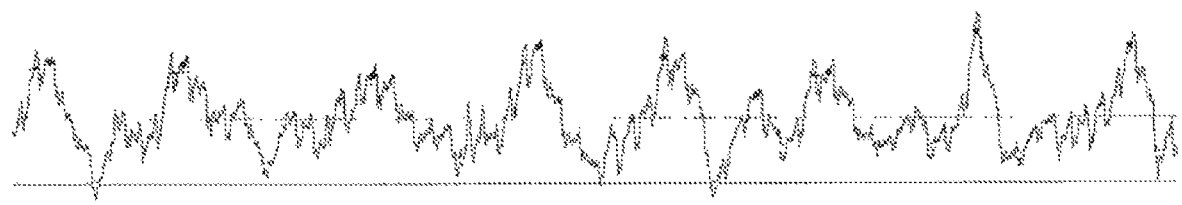

FIG. 10
LEFT LATERAL POSITION
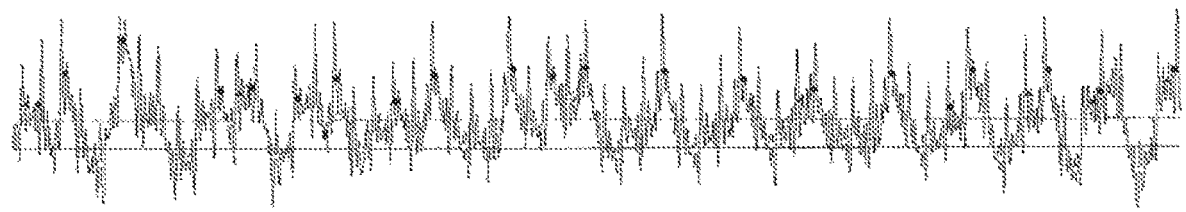
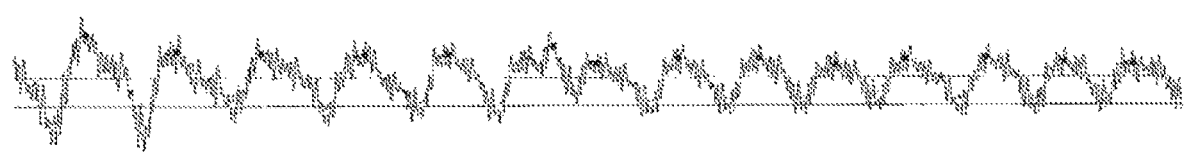

FIG. 13

| | SUPINE POSITION | PRONE POSITION | LATERAL POSITION |
|---|---|---|---|
| CORRELATION IN WAVEFORM OF SENSOR | YES | NO | YES |
| CORRELATION IN PHASE DIFFERENCE BETWEEN SENSORS | YES | YES/NO | NO |
| HOW MUCH WAVEFORM OF HEART BEATS IS SUPERIMPOSED | SMALL | SMALL | LARGE RIGHT SIDE: MEDIUM LEFT SIDE: LARGE |
| WHETHER "FROM VALLEY TO PEAK" -> "FROM PEAK TO VALLEY" IS SAME BETWEEN SENSORS? | SAME | SAME | OPPOSITE/SAME |
| WHETHER "FROM VALLEY TO PEAK" -> "FROM PEAK TO VALLEY" IS "LONG -> SHORT" OR "SHORT -> LONG" | MOSTLY "SHORT -> LONG" | HARD TO MAKE OUT (SOMETIMES SAME) | ----- |

FIG. 14

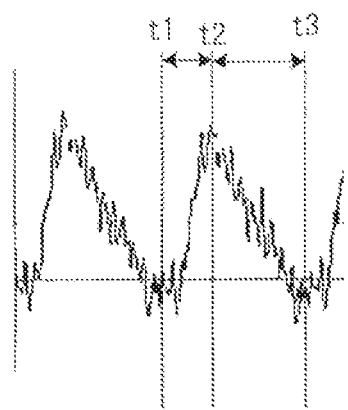

POSTURE DETERMINATION APPARATUS

TECHNICAL FIELD

The present invention relates to a posture determination apparatus.

BACKGROUND ART

Heretofore, there has been known an invention for determining the state of a user on a bed (patient). For example, the detection device disclosed in PTL 1 detects vibrations on a bed and extracts a heart beat vibration signal caused by heart beats of a biological subject. Then, the detection device presumes the posture of the biological subject on the bed based on the heart beat vibration signal extracted.

Meanwhile, the notification device disclosed in PTL 2 acquires the state of a user that includes at least one of: the posture of the user; and the position of the user on a bed or outside the bed. Then, the notification device gives notice according to the state of the user thus acquired.

CITATION LIST

Patent Literature

PTL 1: Japanese Patent Application Publication No. 2011-120667
PTL 2: Japanese Patent Application Publication No. 2016-192998

SUMMARY OF INVENTION

Technical Problem

The present invention provides a posture determination apparatus capable of determining the posture of a user appropriately from a waveform generated by vibrations of the user.

Solution to Problem

A posture determination apparatus of the present invention is characterized by including: at least two vibration sensors capable of detecting vibrations while the user is lying in bed; and a controller configured to calculate multiple waveforms from the multiple vibrations and determine the posture of the user while the user is lying in bed based on the characteristics of the multiple waveforms.

Advantageous Effects of Invention

According to the posture determination apparatus of the present invention, the posture of a user during lying in bed can be determined appropriately as one factor of the state of the user based on multiple waveforms calculated from vibrations.

BRIEF DESCRIPTION OF DRAWINGS

FIG. 7 is a chart illustrating an example of a waveform in the case of a prone position of the first embodiment.
FIG. 10 is a chart illustrating an example of a waveform in the case of a left lateral position of the first embodiment.
FIGS. 11A and 11B are charts illustrating an example of a frequency component of the first embodiment.
FIG. 13 is a chart for explaining a posture determination condition of the second embodiment.
FIG. 14 is a chart for explaining a waveform state of the second embodiment.

DESCRIPTION OF EMBODIMENTS

Hereinbelow, an embodiment for carrying out the present invention is described with reference to the drawings. With the objective of preventing a user from falling off a bed when getting out of the bed, the existing apparatus detects whether or not the user has got out of the bed (whether or not the user is on the bed); however, the apparatus does not detect what posture the user is in when he/she is on the bed.

When the apparatus detects the posture of a user such as a sitting position with his/her soles of feet on a floor, the apparatus sometimes determines whether the user is in a lying position or a sitting position with multiple devices (such as sensors) arranged in a wide range on a bed by the user or the like; however, the apparatus is incapable of determining the orientation of the user (such as a supine position, a prone position, and a lateral position) when the user is lying on the bed.

In order for the apparatus to determine the posture of a user, a medical service worker, a staff, a family, or the like (hereinafter referred to as the caregiver) needs to monitor the user with a camera device or the like additionally installed by the user or the like, or needs to analyze images taken by the apparatus with the camera device or the like. In this case, the caregiver needs to always monitor the user, which places a large burden on the caregiver. In addition, in order to monitor the user, the camera device needs to take images of the user at all times; for this reason, the user sometimes opposes taking images with the camera device in light of privacy concerns.

Against this background, a posture determination apparatus of this embodiment makes it possible to detect the posture of a user as well by simply detecting vibrations while the user is sleeping on the bed.

Note that, throughout this specification, a user indicates a person who uses a bed (or a mattress). In addition to a person who receives treatment due to sickness, a person who receives nursing care in a facility and a person who sleeps on a bed may also be applicable as the user.

1. First Embodiment

[1.1 Overall System]

Figure 1:
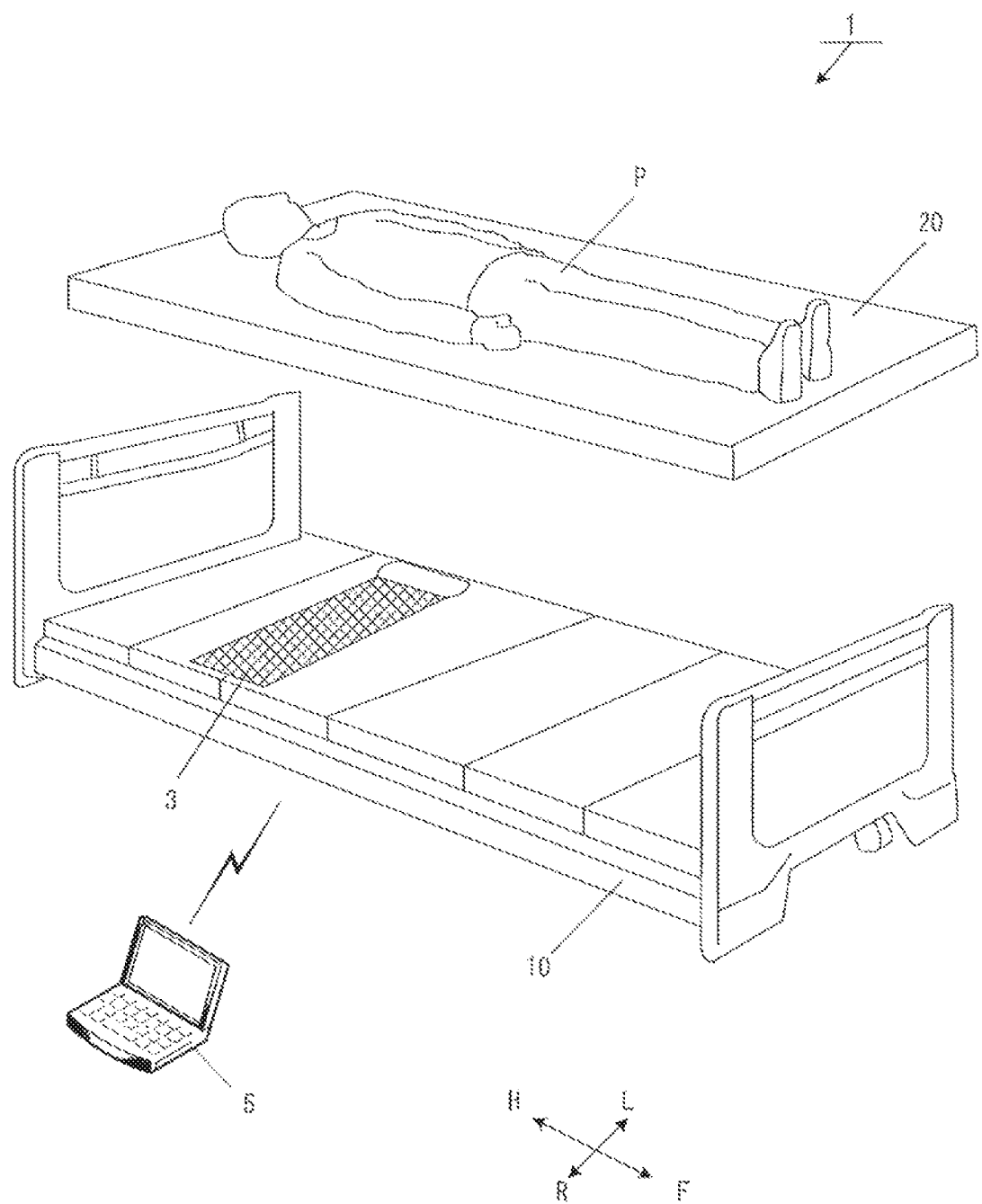
FIG. 1 is a view for explaining the overall configuration of the first embodiment.

FIG. 1 is a view for schematically explaining the overall system 1 in which the posture determination apparatus of the present invention is employed. As illustrated in FIG. 1, the system 1 includes: a detection device 3 placed between a section of a bed 10 and a mattress 20; and a processing device 5 for processing values output from the detection device 3. The system 1 determines the posture of the user with the detection device 3 and the processing device 5.

When a user P is on the bed 10 (or the mattress 20), the detection device 3 detects body vibrations (vibrations generated from a human body) as a biological signal of the user P who is the user. Meanwhile, the processing device 5 calculates biological information values of the user P based on the vibrations detected by the detection device 3.

The processing device 5 may output and display the calculated biological information values (such as a breathing rate, a heart rate, and the amount of activity) as the biological information values of the user P.

Meanwhile, the detection device 3 may be formed integrally with the processing device 5 by arranging a memory, a display, and the like in the detection device 3. Meanwhile, the processing device 5 may be a general-purpose device, and may be a device such as a tablet and a smartphone without being limited to an information processor such as a computer. Meanwhile, if the detection device 3 has a communication function, the detection device 3 may be connected to (communicate with) a server apparatus instead of the processing device 5.

Meanwhile, the user may be a sick person who is under medical treatment or may be a person who needs nursing care. In addition, the user may be a healthy person who needs no nursing care, and may be an elderly person or a child, and may be a disabled person, and may be an animal other than a human.

Here, the detection device 3 is a device in the form of a thin sheet, for example. Thereby, even when the detection device 3 is placed between the bed 10 and the mattress 20, it is possible to use the detection device 3 without making the user P feel a sense of discomfort. This enables the detection device 3 to detect the state of the user on the bed for a long time.

Note that the detection device 3 has only to detect vibrations of the user P. For example, an actuator with strain gauge or a load cell which is disposed on legs etc. of the bed 10 for measuring a load may be used as the detection device 3. Alternatively, a device such as a smartphone which is placed on the bed 10 or an acceleration sensor which is built in a tablet etc. may be used as the detection device 3.

In addition, in FIG. 1, a direction toward the head side of the bed 10 (the mattress 20) is defined as a direction H, and a direction toward the foot side thereof is defined as a direction F. Further, in FIG. 1, in a state where the user P is in a supine position on the bed 10, a direction toward the left side of the user P is defined as a direction L, and a direction toward the right side of the user P is defined as a direction R.

[1.2 Configuration]

The configuration of the system 1 is described with reference to FIGS. 2 to 4. The system 1 in this embodiment includes the detection device 3 and the processing device 5. Function units other than a detection unit 110 may be included in any one of the detection device 3 and the processing device 5. Either one of the detection device 3 and the processing device 5 implements the functions of the function units other than the detection unit 110. The detection device 3 and the processing device 5 function as a posture determination apparatus by combining the detection device 3 and the processing device 5 together.

The system 1 (posture determination apparatus) includes: a controller 100; the detection unit 110; a first calculation unit 120; a second calculation unit 130; a third calculation unit 135; a determination unit 140; a memory 150; an input unit 160; and an output unit 170.

The controller 100 is configured to control the operation of the system 1. The controller 100 is a controller such as a CPU (Central Processing Unit). The controller 100 implements various kinds of processing by retrieving various programs stored in the memory 150 and executing the various programs. Note that, although the system in this embodiment has one controller 100 as a whole, the controller 100 may be provided in each of the detection device 3 and the processing unit 5 as will be described in FIG. 4 later.

The detection unit 110 is configured to detect vibrations on the detection device 3 and acquire vibration data. For example, the detection unit 110 of this embodiment uses a pressure change detection sensor to detect vibrations (body vibrations) generated based on the movement of the user etc. In addition, the detection unit 110 acquires vibration data based on the vibrations thus detected. The detection unit 110 outputs the vibration data to the first calculation unit 120, the second calculation unit 130, and the third calculation unit 135. Note that the vibration data may be analog vibration data or may be digital vibration data.

Alternatively, the detection unit 110 may detect vibrations of the user and acquire vibration data using a pressure sensor, for example. Still alternatively, the detection unit 110 may be provided with a microphone instead of the pressure sensor. The detection unit 110 may acquire a biological signal based on sound collected by the microphone and acquire vibration data from the biological signal. Still alternatively, the detection unit 110 may acquire vibration data from output values of an acceleration sensor, a capacitance sensor, and a load sensor. In this way, the detection unit 110 may use any method to acquire a biological signal (body vibrations indicating the body movement of the user).

The first calculation unit 120 is configured to acquire a biological signal of the user from the vibration data, and calculate biological information values (such as a breathing rate, a heart rate, and the amount of activity). In this embodiment, the first calculation unit extracts a breathing component and a heart beat component from the vibration (body vibration) data acquired by the detection unit 110. The first calculation unit 110 may obtain a breathing rate and a heart rate from the extracted breathing component and heart beat component based on a breathing interval and a heart beat interval. Alternatively, the first calculation unit 120 may analyze (e.g. Fourier transform) the periodicity of the vibration data and calculate a breathing rate and a heart rate from the peak frequency.

As a method of calculating such biological information values of the user, the determination method described in Japanese Patent Application Publication No. 2010-264193 (Title of Invention: Sleep State Determination Apparatus, Program, and Sleep State Determination System, Filing Date: May 18, 2009) or in Japanese Patent Application Publication No. 2015-12948 (Title of Invention: Sleep Evaluation Apparatus, Sleep Evaluation Method, and Sleep Evaluation Program, Filing Date: Jul. 4, 2013) can be incorporated. The entire content of this patent application is incorporated herein by reference.

The second calculation unit 130 is configured to convert the analog vibration data, input from the detection unit 110, into a digital voltage signal at a predetermined sampling interval, and calculate waveform data indicating a waveform of body vibrations (vibration waveform).

The third calculation unit 135 is configured to calculate frequency distribution from the waveform data. For example, the third calculation unit 135 calculates frequency distribution from a frequency component which is obtained by applying Fast Fourier Transform (FFT) to the waveform data, calculated by the second calculation unit 130. Note that the third calculation unit 135 may calculate frequency distribution directly based on the vibration data output from the detection unit 110.

The determination unit 140 is configured to determine the state of the user. For example, the determination unit 140 determines the state of the user using at least one of: the vibration data acquired by the detection unit 110; the biological information values calculated by the first calculation unit 120; the value acquired by the load sensor separately provided to the bed 10, the waveform data calculated by the second calculation unit 130; the frequency distribution calculated by the third calculation unit 135; and the like. The determination unit 140 may determine the state of the user using multiple sets of data, values, and the like in combination.

In this embodiment, the determination unit 140 determines the posture of the user (which of a supine position, a prone position, and a lateral position the user is in) on the bed as the state of the user. The determination unit 140 may also determine the posture of the user, such as a sitting position with his/her soles of feet on the floor, and the state of the user other than his/her posture (e.g. whether the user gets out of the bed or on the bed).

The memory 150 is configured to store therein various kinds of data and programs for the system 1 to operate. The controller 100 implements various functions by retrieving these programs and executing the programs. Here, the memory 150 is constituted of a semiconductor memory (such as an SSD (Solid State Drive) and an SD card (registered trademark)), a magnetic disk device (such as an HDD (Hard Disk Drive)), or the like. Meanwhile, the memory 150 may be a built-in storage device, or may be an attachable and detachable external storage device. Alternatively, the memory 150 may be a storage area of an external server such as a cloud server.

The memory 150 includes a vibration data storage area 152 and a waveform data storage area 154. The vibration data storage area 152 and the waveform data storage area 154 are respectively assigned to areas inside the memory 150.

The vibration data storage area 152 is configured to store therein the vibration data output from the detection unit 110. Here, the vibration data is stored for every predetermined period of time. For example, the vibration data is stored at a relatively short interval such as for every second or for every five seconds, or stored at a relatively long interval such as for every thirty seconds, for every one minute, or for every five minutes.

The waveform data storage area 154 is configured to store the waveform data (waveform) of vibrations, calculated by the second calculation unit 130, based on the vibration data output from the detection unit 110 or the vibration data stored in the vibration data storage area 152. Note that, although the description in this embodiment is given of the case where the waveform data is stored in the waveform data storage area 154, the second calculation unit 130 may calculate waveform data every time when needed. Meanwhile, the waveform data may be temporarily stored in the waveform data storage area 154 or may be stored accumulatively.

The input unit 160 is configured to accept manipulation from the user. For example, the input unit 160 accepts various manipulation inputs from the user including a manipulation input indicating start of acquiring vibrations of the user and a manipulation input indicating adjustment of the sensitivity of the detection unit 110. Examples of the input unit 160 include a keyboard, a mouse, and a touch panel.

The output unit 170 is configured to output various kinds of information. Examples of the output unit include a liquid crystal display device, a light emitting member such as an LED, a speaker for audio and voice output, and an interface for outputting data to another recording medium. Alternatively, the input unit 160 and the output unit 170 may be formed integrally. For example, one touch panel may function as both the input unit 160 and the output unit 170.

Here, in the above configuration, the first calculation unit 120, the second calculation unit 130, the third calculation unit 135, and the determination unit 140 are implemented mainly by software (program). For example, the controller 100 retrieves software stored in the memory 150 and executes the software. As a result, the controller 100 implements the various functions of the configuration.

Specifically, the controller 100 has the various functions of the configuration by retrieving a program implementing the first calculation unit 120, the second calculation unit 130, the third calculation unit 135, and the determination unit 140 and executing the program.

Figure 2:
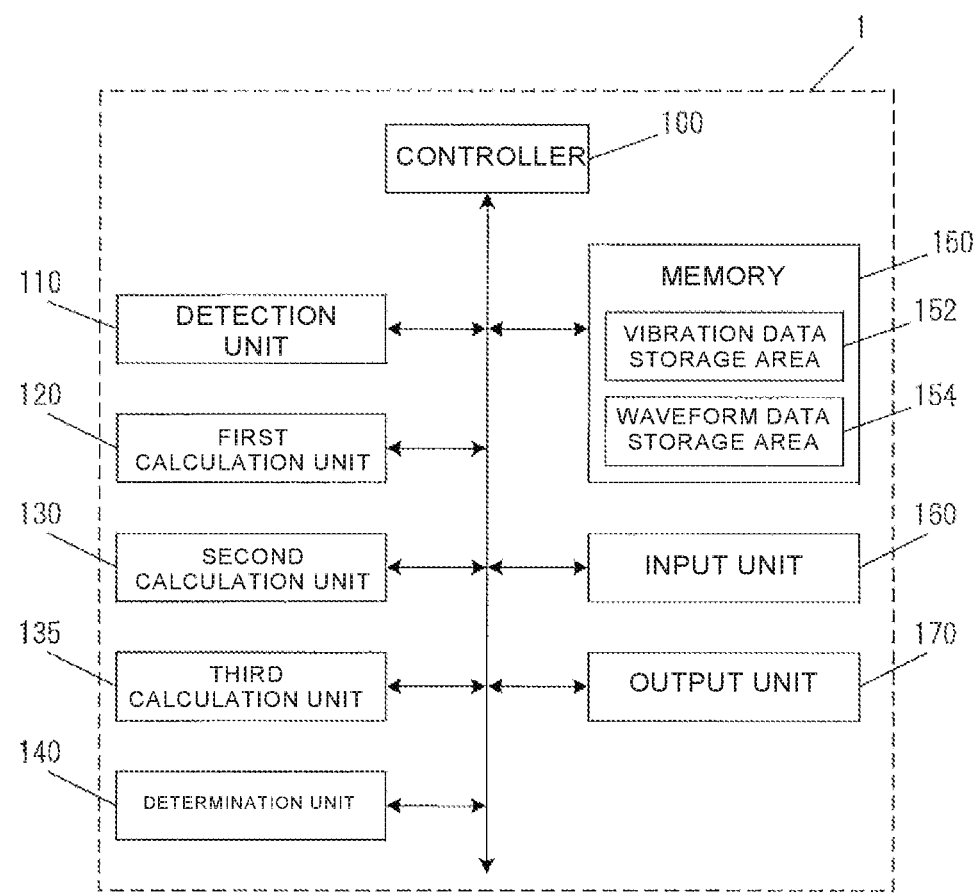
FIG. 2 is a diagram for explaining the configuration of the first embodiment.

Meanwhile, FIG. 2 explains the configuration of the posture determination apparatus of the system 1. For example, this configuration may be implemented by one device capable of detecting vibrations, or alternatively, the posture determination apparatus may be constituted separately of the detection device 3 and the processing device 5 as illustrated in FIG. 1. Still alternatively, the posture determination apparatus may be implemented using, instead of the processing device 5, an external server capable of providing the same service as the processing device.

The posture determination apparatus of the system 1 in the case where the system 1 of FIG. 2 is constituted of the detection device 3 and the processing device 5 of FIG. 1 is described with reference to FIG. 3. The detection device 3 includes: a controller 300; a detection unit 320 which is a sensor; a memory 330; and a communication unit 390.

In addition, the controller 300 functions as a first calculation unit 310 by executing software (program) stored in the memory 330. The detection unit 320 is configured to output vibration data based on detected vibrations.

The first calculation unit 310 is configured to calculate biological information values based on the vibration data. Then, the detection device 3 stores the biological information values in biological information value data 340, and sends the biological information values to the processing device 5 via the communication unit 390. The detection device 3 also sends the vibration data, detected by the detection unit 320, to the processing device 5 via the communication unit 390.

The sending of the vibration data from the detection device 3 to the processing device 5 and the storing of the biological information values (biological information) in the biological information value data 340 may be carried out in real time or at every predetermined period.

Note that the detection unit 320 is equal to the detection unit 110 of FIG. 2. Here, the detection unit 320 is described using FIG. 4.

Figure 4:
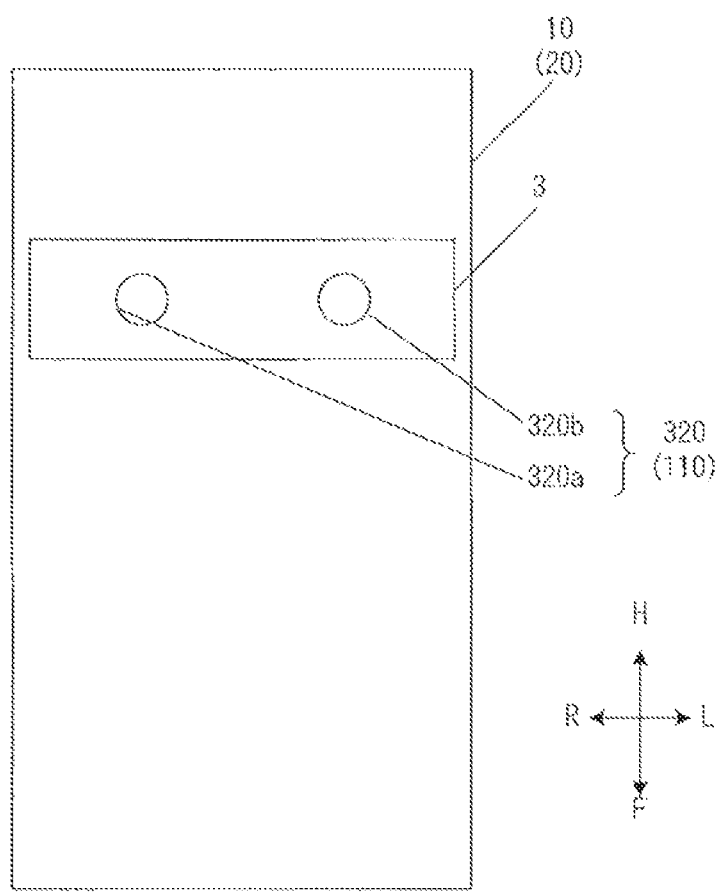
FIG. 4 is a diagram for explaining a sensor of the first embodiment.

FIG. 4 is a diagram of the bed 10 (mattress 20) seen from above. In FIG. 4, a direction toward the upper side is equal to the direction H in FIG. 1, and a direction toward the lower side is equal to the direction F in FIG. 1. In addition, in FIG. 4, a direction toward the right side is equal to the direction L in FIG. 1, and a direction toward the left side is equal to the direction R in FIG. 1.

The detection device 3 is placed between the bed 10 and the mattress 20 or on the mattress 20. The detection device 3 is preferably placed near the back of the user, and is thus placed at least in a direction closer to the H side (the head side of the user) than the center of the bed 10 (mattress 20).

In addition, a sensor (detection unit 110/320) is built in the detection device 3. For example, the sensor is a vibration sensor capable of detecting vibrations (body vibrations) of the user. Further, at least two sensors are arranged in the detection device 3. For example, in FIG. 4, two sensors (vibration sensors 320a and 320b) are arranged on the right and left of the detection device 3.

The vibration sensor 320a is disposed away from the vibration sensor 320b. The distance between the vibration sensor 320a and the vibration sensor 320b may be any size as long as the user can be situated on the sensors, for example, and the distance between the two sensors is preferably about 15 to 60 cm.

Figure 3:
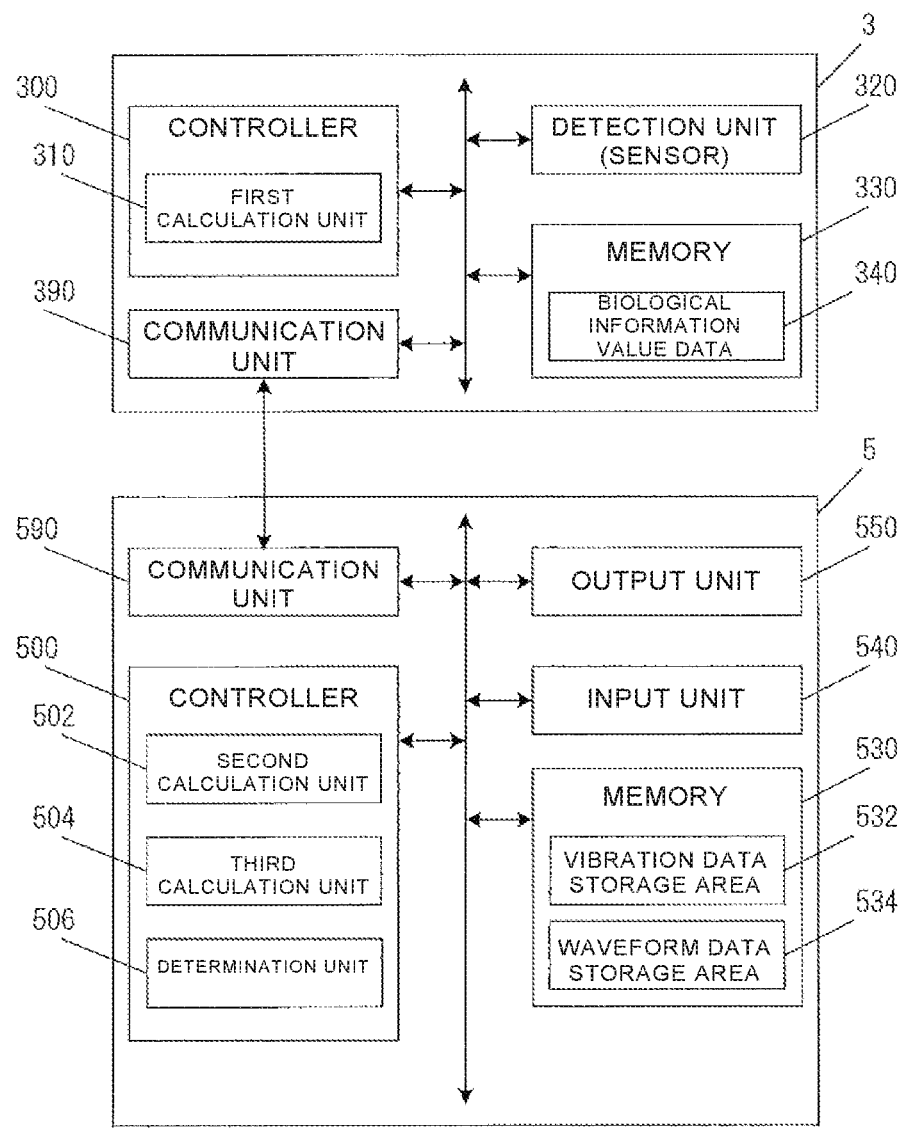
FIG. 3 is another diagram for explaining the configuration of the first embodiment.

Meanwhile, the first calculation unit 310 in FIG. 3 is equal to the first calculation unit 120 in FIG. 2. In addition, the communication unit 390 is an interface capable of being connected to (communicating with) a network (such as LAN/WAN), for example.

The processing device 5 includes: a controller 500; a memory 530; an input unit 540; an output unit 550; and a communication unit 590. The processing device 5 receives the vibration data from the detection device 3 via the communication unit 590. The processing device 5 stores the received vibration data in a vibration data storage area 532.

The controller 500 functions as a second calculation unit 502, a third calculation unit 504, and a determination unit 506 by executing software (program) stored in the memory 530. In addition, waveform data calculated by the second calculation unit 502 is stored in a waveform data storage area 534.

Note that the second calculation unit 502 is equal to the second calculation unit 130 in FIG. 2. The third calculation unit 504 is equal to the third calculation unit 135 in FIG. 2. The determination unit 506 is equal to the determination unit 140 in FIG. 2. The input unit 540 is equal to the input unit 160 in FIG. 2. The output unit 550 is equal to the output unit 170 in FIG. 2. The memory 530 is equal to the memory 150 in FIG. 2.

[1.3 Processing Flow]

Posture determination processing in this embodiment is described with reference to FIG. 5. The posture determination processing is processing executed by the controller 100 (determination unit 140).

First, the controller 100 (determination unit 140) acquires vibration data (Step S102). Specifically, the determination unit 140 acquires the vibration data by retrieving the vibration data from the vibration data storage area 152 or by receiving the vibration data from the detection unit 110.

Subsequently, the determination unit 140 determines the posture of the user based on the vibration data. In this event, the determination unit 140 determines the posture of the user based on the correlation between the sensors and the correlation in each sensor. Here, the correlation between the sensors indicates the correlation between multiple data output from the multiple sensors, and the correlation in each sensor indicates the correlation between multiple data output from one sensor.

First, the second calculation unit 130 calculates a waveform from the vibration data, and outputs it as waveform data (Step S104). The second calculation unit 130 outputs waveform data for each vibration sensor. For example, in FIG. 4, there are two vibration sensors (the vibration sensors 320a and 320b). Accordingly, the second calculation unit 130 outputs waveform data for each vibration sensor. The second calculation unit 130 outputs two sets of waveform data.

In addition, the second calculation unit 130 may store the waveform data in the waveform data storage area 154 or may output it to the output unit 170. In the case where the output unit 170 is a display device, the output unit 170 displays the waveform data.

Then, based on the sets of waveform data, the determination unit 140 determines whether or not the correlation between the sensors exists (Step S106). For example, as the correlation between the sensors, the determination unit 140 determines whether or not there is a similarity between the sets of waveform data that are output from the two sensors (the vibration sensors 320a and 320b in FIG. 4, for example).

The determination unit 140 obtains the correlation between the sensors by applying a cross-correlation function to the two sets of waveform data. By using the cross-correlation function, the determination unit 140 can output any of values normalized from "0" to "1" based on the similarity between the two sets of waveform data. The value output using this cross-correlation function varies depending on the similarity between the two sets of waveform data. For example, in the case where the value returned by the cross-correlation function is "1", the two sets of waveform data completely match each other and exhibit the maximum similarity. On the other hand, in the case where the value returned by the cross-correlation function is "0", the two waveforms do not match each other at all and exhibit the minimum similarity.

In addition, when determining whether or not there is a correlation between the two sets of waveform data, the determination unit 140 determines whether or not the output value of the cross-correlation function exceeds a threshold. For example, in the case where the threshold is set at "0.7", the determination unit 140 determines that there is no correlation between the two sets of waveform data if the output value of the cross-correlation function is equal to or smaller than "0.7". The determination unit 140 determines that there is a correlation between the two sets of waveform data if the output value of the cross-correlation function exceeds "0.7". In other words, the determination unit 140 determines that the correlation between the sensors exists if there is a correlation between the two sets of waveform data.

Next, if the correlation between the sensors exists (Step S106: Yes), the determination unit 140 determines that the posture of the user is "either a supine position or a prone position" (Steps S116 to S120). Note that, since the user usually takes a prone position during sleep for an extremely short period of time, the determination unit 140 may only determine that the posture of the user is "either a supine position or a prone position". However, a prone position causes a high risk of suffocation and is reported to be associated with sudden infant death syndrome. In addition, an automatic operation of an electric bed needs to be prohibited while the user is in a prone position, for example. Thus, for the purpose of distinguishing a supine position and a prone position from each other, the determination unit 140 may determine whether or not the posture of the user is "a supine position" and whether or not the posture of the user is "a prone position".

The determination unit 140 determines whether or not the correlation in each sensor exists (Step S106: Yes→Step S116). In this Step, the determination unit 140 determines whether or not the correlation in each sensor exists. For example, the determination unit 140 determines whether or not the correlation in each sensor exists by evaluating the strength of periodicity in waveform data. As an example, the determination unit 140 determines whether or not the correlation exists by applying an auto-correlation function to waveform data of one sensor. The auto-correlation function outputs any of values normalized from "0" to "1" based on the strength of periodicity in the waveform of a single sensor. For example, in the case where the value returned by the auto-correlation function is "1", the determination unit 140 determines that the waveform data is output completely periodically and the perfect correlation in the sensor exists. On the other hand, in the case where the value returned by the auto-correlation function is "0", the determination unit 140 determines that no correlation in the sensor exists.

Meanwhile, the determination unit 140 may calculate the strength of periodicity as any of values normalized from "0" to "1" by using a method such as the Fourier transform and the Chi-square periodogram and determine the correlation in each sensor based on this value.

Besides, when determining whether or not the correlation in one waveform data exists, the determination unit 140 may determine whether or not the output value of the auto-correlation function exceeds a threshold. For example, in the case where the threshold is set at "0.7", the determination unit 140 determines that there is no correlation in the waveform data calculated (one vibration data detected) if the output value of the auto-correlation function is equal to or smaller than "0.7". The determination unit 140 determines that there is a correlation in the waveform data if the output value of the auto-correlation function exceeds "0.7".

If the determination unit 140 determines that the correlation in the sensor exists, the determination unit 140 determines that the posture of the user is "a supine position" (Step S116: Yes→Step S118). On the other hand, if the determination unit 140 determines that no correlation in the sensor exists, the determination unit 140 determines that the posture of the user is "a prone position" (Step S116: No→Step S120).

Meanwhile, if the determination unit 140 determines that no correlation between the sensors exists in Step S106 (Step S106: No), the determination unit 140 determines that the posture of the user is "a lateral position" (Step S110). Note that, the determination unit 140 may simply determine that the posture of the user is "a lateral position"; instead, in order to distinguish "a right lateral position" and "a left lateral position" from each other, the determination unit 140 may further determine whether or not the posture of the user is "a right lateral position" and whether or not the posture of the user is "a left lateral position" (Step S114). Since the caregiver checks whether or not the user has changed his/her body position or, in the case where the user's body is partially paralyzed, for example, the caregiver needs to pay attention so that the user may not sleep in a lateral position with the paralyzed side down, the determination unit 140 may determine whether or not the posture of the user is "a right lateral position" and whether or not the posture of the user is "a left lateral position".

In this case, a heart rate signal obtained when the user is in a left lateral position is larger than a heart rate signal obtained when the user is in a right lateral position. Accordingly, the determination unit 140 determines that the posture of the user is "a left lateral position" if the heart rate signal has a magnitude equal to or larger than a predetermined threshold (if a high-frequency signal is extracted).

Various methods are conceivable as a method for the determination unit 140 to determine the magnitude of a heart rate signal. For example, the determination unit 140 can determine the magnitude of the heart rate signal using the ratio of a frequency component, which corresponds to a breathing signal, to a frequency component, which corresponds to the heart rate signal, and the strength of a data signal having been subjected to high-pass filter processing.

In this way, the posture determination apparatus of this embodiment can determine the posture (the posture during sleep) of the user based on vibration data.

Meanwhile, for the sake of convenience of description, the determination unit 140 of this embodiment determines whether or not the correlation between the sensors or the correlation in each sensor exists based on the waveform data calculated by the second calculation unit 130. While not limited thereto, the determination unit 140 may determine the correlation between the sensors or the correlation in each sensor simply based on the vibration data, for example. In this case, the determination unit 140 does not have to execute the processing in Step S104.

Meanwhile, the determination unit 140 determines the posture of the user by calculating the waveform data from the vibration data of the user; while not limited thereto, the determination unit 140 may determine the posture by evaluating the shape of frequency distribution, for example. In this case, although the determination unit 140 can achieve better accuracy if making a comprehensive evaluation of the shape of frequency distribution of vibrations acquired by two or more sensors, the number of sensors for acquiring vibrations may be one.

As an example, the user's posture determination processing executed by the determination unit 140 using frequency analysis is described with reference to FIG. 6. As in FIG. 5, the determination unit 140 acquires vibration data from the detection unit 110 (Step S152), and the second calculation unit 130 calculates (outputs) waveform data (Step S154).

Subsequently, the third calculation unit 135 calculates frequency distribution of the waveform data output from the second calculation unit 130 (Step S156). For example, if no high-frequency component is calculated in the frequency distribution, the determination unit 140 identifies the posture of the user as "a lateral position".

Since the relation between the position of a heart and the position of the sensor differs depending on the posture of the user, body organs (such as muscles, fat, bones, and internal organs) existing between them also differs. Accordingly, how vibrations are transmitted from the user to the sensor also varies, which results in a difference in the frequency component measured by the system 1.

The movement of the heart and the direction in which a thoracoabdominal part moves during breathing are fixed. For example, when the user is in a supine position, the thoracoabdominal part moves greatly in the direction perpendicular to the sensor (the detection unit 110) during breathing. Meanwhile, when the user is in a lateral position, the thoracoabdominal part moves greatly in the direction parallel to the sensor (the detection unit 110). In this way, frequency distribution differs from one posture of the user to another. Accordingly, the determination unit 140 can determine the posture by storing frequency distribution of each posture in advance and comparing the frequency distribution actually extracted with the frequency distribution stored for each posture.

For example, when the user is in a lateral position, a frequency component higher than a heart beat component is less likely to be detected (excluding integral multiplication of a frequency corresponding to the heart beat component). Thus, if there is little frequency component which is higher than the heart beat component, the determination unit 140 can determine that the posture of the user is "a lateral position".

Note that, although the third calculation unit 135 calculates the frequency distribution from the waveform data in the above description, the third calculation unit may calculate the frequency distribution directly from the vibration data. In this case, Step S154 is not executed.

[1.4 Posture Determination Condition]

Here, the determination unit 140 may execute the posture determination processing described above while the user is on the bed. Alternatively, the determination unit 140 may execute the posture determination processing once the state of the user or the bed satisfies a predetermined condition. Hereinbelow, the body movement of the user is used as a condition of making the determination unit 140 execute the posture determination processing. Here, the body movement of the user indicates a change in the posture of the user such as the rolling over of the user.

(1) Determination Unit 140 Determines Posture of User for Every Section

The determination unit 140 divides the time period, for which the determination unit 140 determines the posture of the user, into multiple sections. For example, in the section with no body movement, the determination unit 140 determines that the user keeps taking the same posture. Then, the determination unit 140 makes an output of "the user takes the same posture".

In this case, the determination unit 140 may analyze (apply the result of the posture determination processing to) sections with no body movement of the user at the same time. Alternatively, the determination unit 140 may aggregate the result of the posture determination processing obtained for a certain section (e.g. for every three minutes). If there are section(s) with no body movement in that certain section, the determination unit 140 outputs the posture determination result, which is returned most in the section(s) with no body movement, as the result of the posture determination processing in that section.

(2) Determination Unit 140 Determines Posture of User Only in Section where No Body Movement Occurs The determination unit 140 determines the posture of the user only in the section where no body movement of the user occurs. For example, if the body movement of the user is detected by the detection unit 110, the determination unit 140 stops executing the posture determination processing. In addition, after the body movement of the user is detected by the detection unit 110, the determination unit 140 executes the posture determination processing again after a predetermined period of time elapses since body movement is no longer detected (e.g. after 10 seconds since body movement is no longer detected).

[1.5 Description Based on Waveform]

Here, a method for the determination unit 140 to determine the posture of the user is described based on waveforms. Waveforms illustrated in FIGS. 7 to 10 are waveforms based on vibrations detected by the two vibration sensors. In the waveforms in FIGS. 7 to 10, the lateral axis indicates the time while the longitudinal axis indicates a voltage value, and these waveforms each indicate a waveform based on vibrations detected by the detection unit 110. Note that the method for the determination unit 140 to determine the posture of the user based on waveforms is described for the sake of convenience of description. As another method for determining the posture, the determination unit 140 may determine the posture of the user by detecting a trend from time-series vibration data, for example.

In the two waveforms illustrated in FIG. 7, no correlation is found in the waveform of each sensor and the same shape is not repeated. That is to say, these waveforms are waveforms indicating that the posture of the user is a prone position (Step S120 in FIG. 5).

Figure 8:
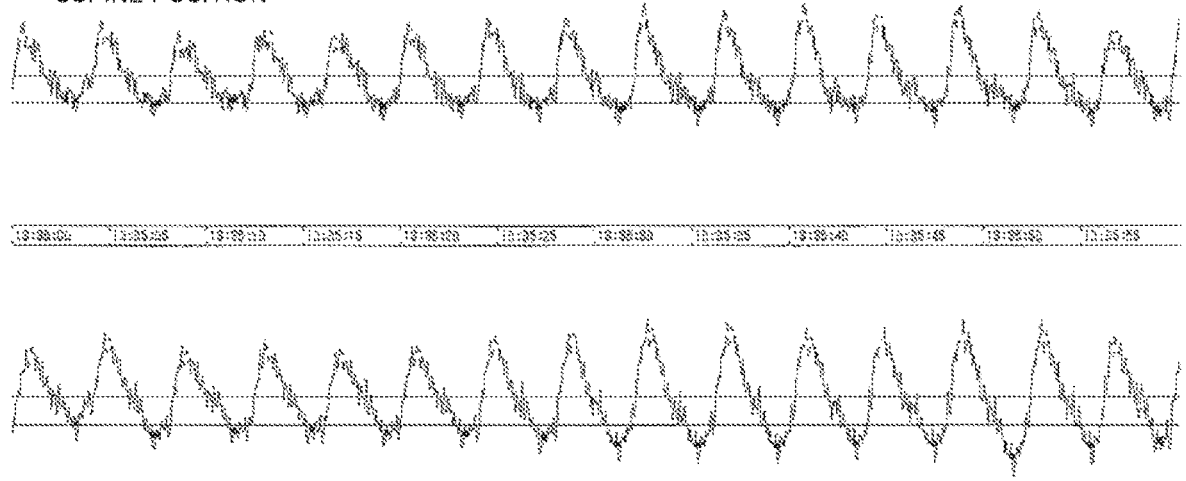
FIG. 8 is a chart illustrating an example of a waveform in the case of a supine position of the first embodiment.

In the two waveforms illustrated in FIG. 8, there is a correlation between the waveforms of the sensors and there is also a correlation in the waveform of each sensor. That is to say, these waveforms are waveforms indicating that the posture of the user is a supine position (Step S118 in FIG. 5).

Figure 9:
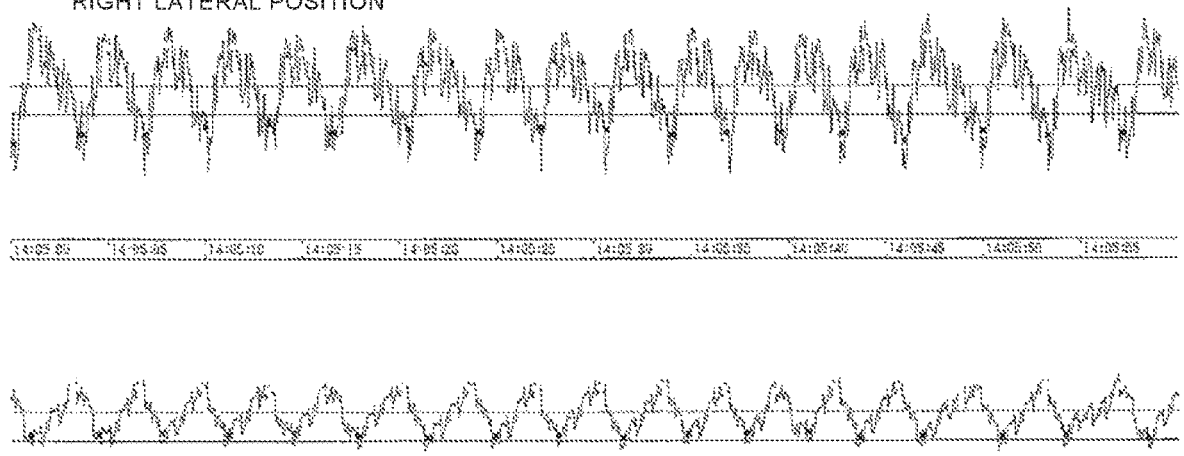
FIG. 9 is a chart illustrating an example of a waveform in the case of a right lateral position of the first embodiment.

The two waveforms illustrated in each of FIGS. 9 and 10 are waveforms with no correlation between the sensors. That is to say, these waveforms are waveforms indicating that the posture of the user is a lateral position (Step S110 in FIG. 5). When FIGS. 9 and 10 are compared with each other, the waveforms illustrated in FIG. 10, which are the waveforms of a left lateral position, more remarkably exhibit a high-frequency signal due to heart beats.

Figure 11A:
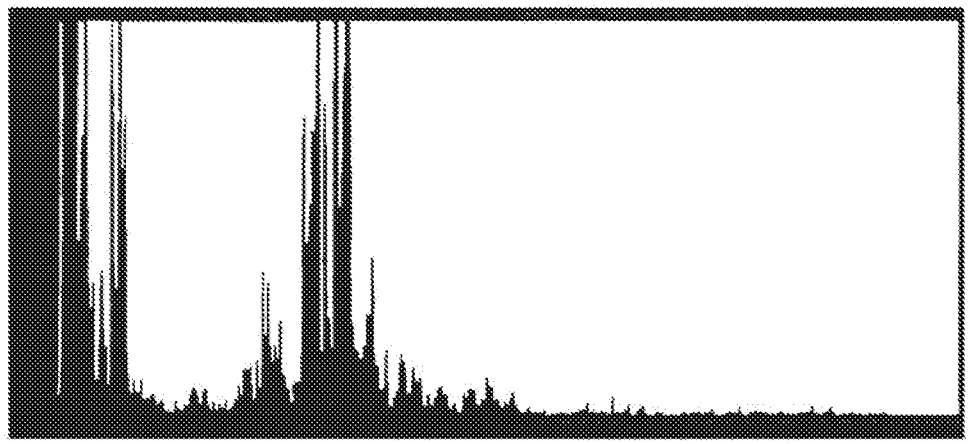
[FIGS. 11A and 11B]
Figure 11B:
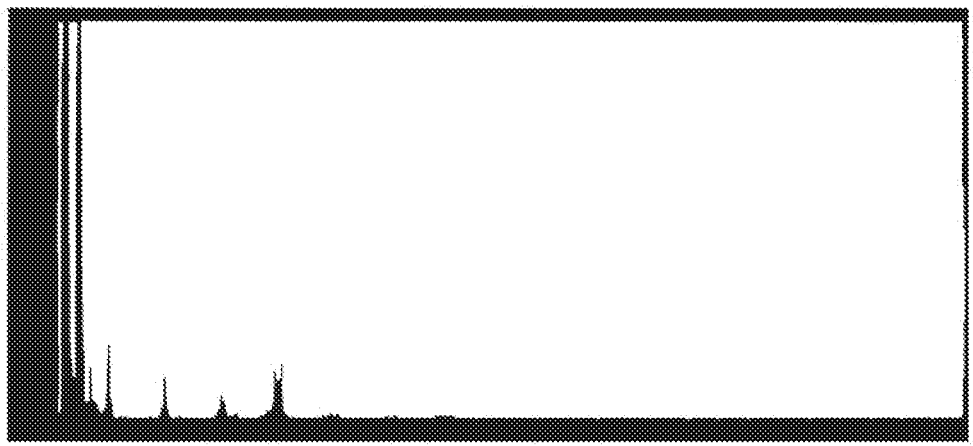

FIGS. 11A and 11B are graphs of frequency distribution obtained from the waveforms. FIGS. 11A and 11B are graphs indicating that the frequency distribution is obtained in Step S156 of FIG. 6, in which FIG. 11A is a graph indicating a supine position while FIG. 11B is a graph indicating a lateral position. In this manner, the determination unit 140 can determine the posture of the user by further obtaining the frequency distribution from the waveforms (vibration data).

2. Second Embodiment

A second embodiment is described. The second embodiment is an embodiment in which the posture of the user is determined based on multiple posture determination conditions.

Figure 5:
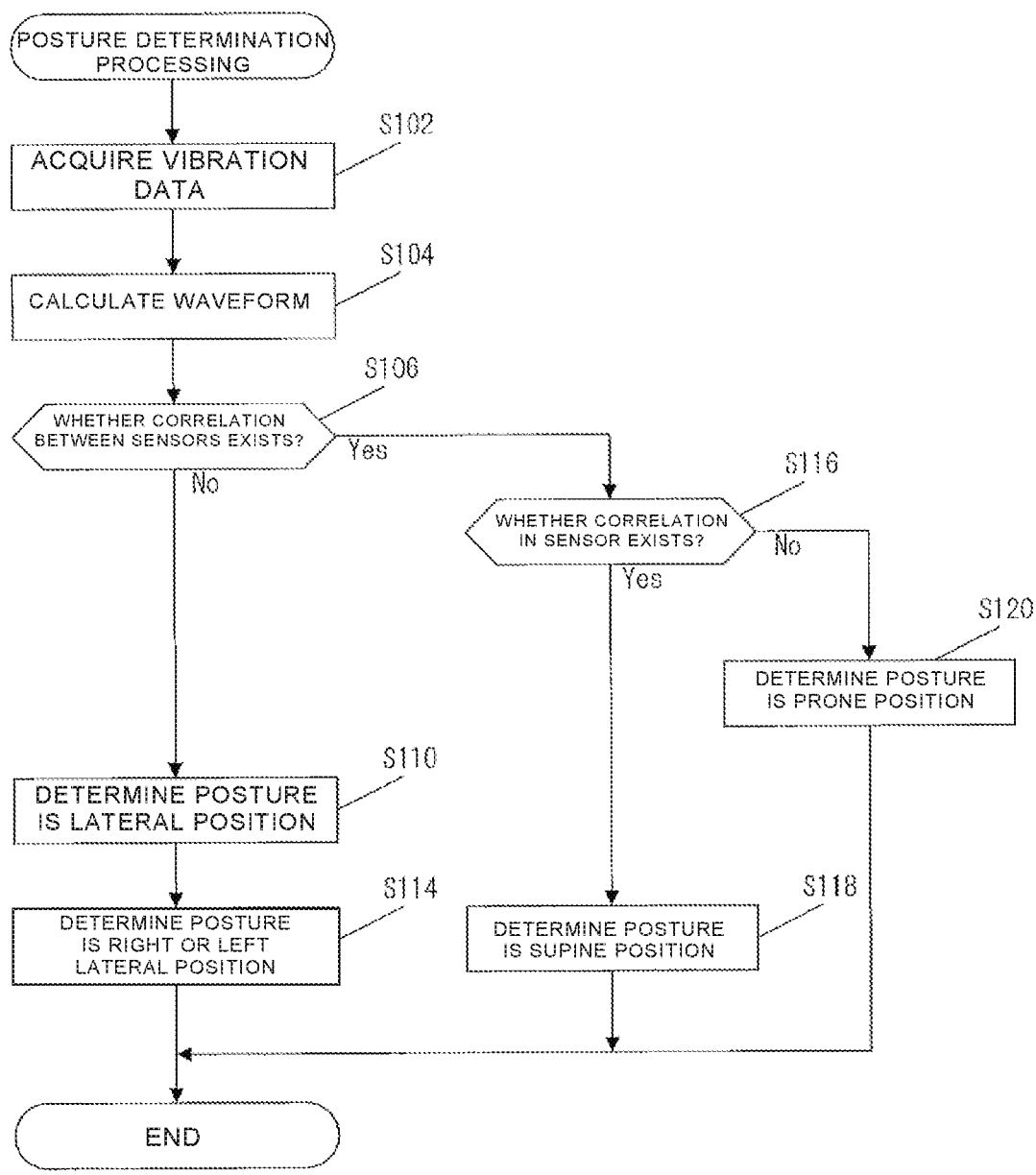
FIG. 5 is a chart for explaining posture determination processing of the first embodiment.
Figure 6:
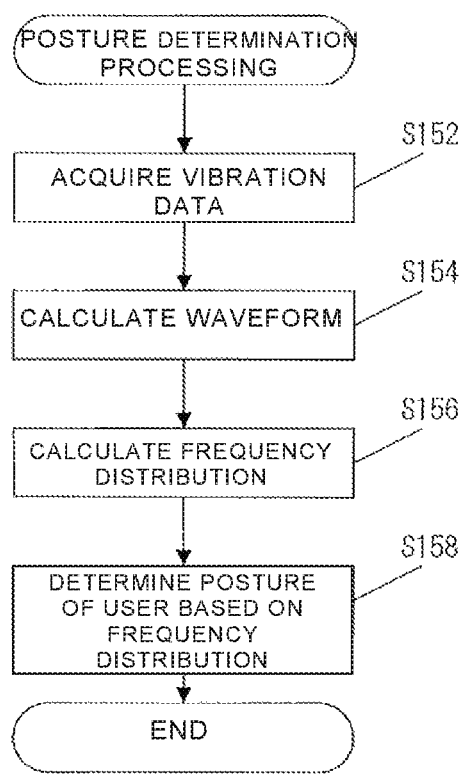
FIG. 6 is another chart for explaining the posture determination processing of the first embodiment.
Figure 12:
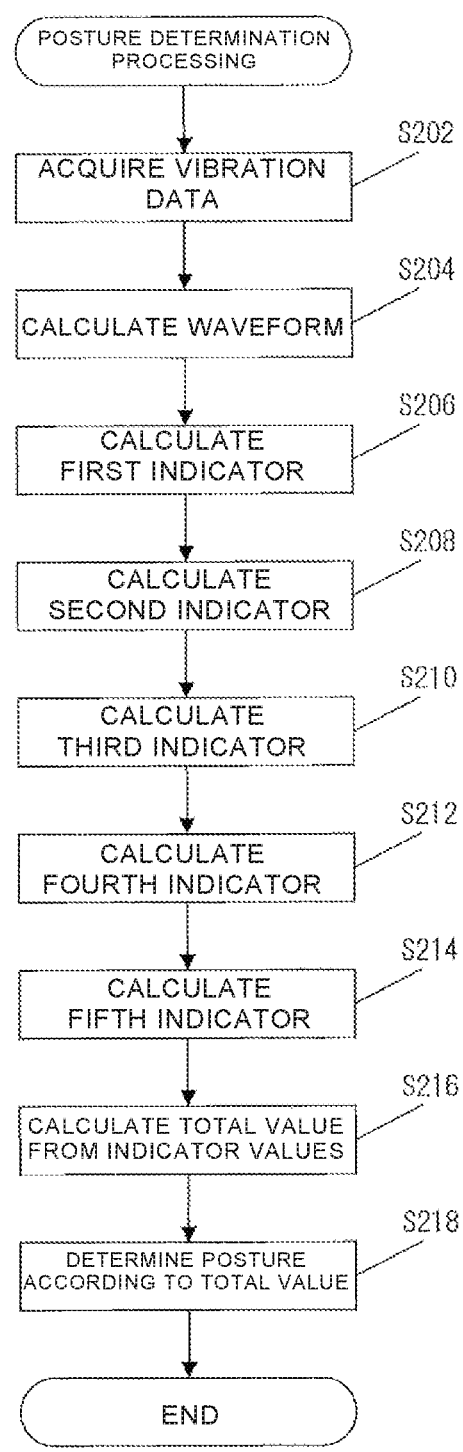
FIG. 12 is a chart for explaining posture determination processing of a second embodiment.

Note that the second embodiment is an embodiment implemented by replacing the operation flow of FIG. 5 in the first embodiment with an operation flow of FIG. 12. In this embodiment, parts having the same configuration and the like as the first embodiment are not described.

First, the determination unit 140 acquires vibration data (Step S202). Subsequently, the second calculation unit 130 calculates a waveform (Step S204). Then, the determination unit 140 calculates an indicator (value) for each condition (Steps S206 to S214). The determination unit 140 calculates a total value from the indicator values thus calculated (Step S216).

As the total value, the determination unit 140 calculates a total value corresponding to each of "a supine position", "a prone position", and "(right and left) lateral positions". Then, the determination unit 140 determines the posture with the largest total value as the posture of the user.

Here, the determination unit 140 calculates an indicator value for each condition in Steps S206 to S214. A method of calculating these indicator values is described with reference to FIG. 13.

(1) Calculation of First Indicator (Step S206)

The determination unit 140 calculates a first indicator value calculated from the correlation in the waveform of each sensor. First, the determination unit 140 calculates a value of an auto-correlation function based on the waveform of each sensor by using the method described in the first embodiment.

Then, the determination unit 140 calculates the first indicator value by weighting the output value of the auto-correlation function. Here, a weighting method executed by the determination unit 140 is described.

The chart of FIG. 13 is a chart illustrating the waveform characteristics of the sensors for each posture of the user. For example, the correlation in the waveform of each sensor is "YES" when the posture of the user is "a supine position", "YES" when the posture of the user is "a lateral position", and "NO" when the posture of the user is "a prone position".

Here, the determination unit 140 executes the auto-correlation function to output any of values between "0 and 1". Here, when the correlation in the waveform of each sensor is "YES" ("a supine position" or "a lateral position") in FIG. 13, the determination unit 140 sets the output value as the first indicator value as it is. On the other hand, when the correlation in the waveform of each sensor is "NO" in FIG. 13, the determination unit 140 sets, as the first indicator value, a value obtained by subtracting the output value of the auto-correlation function from the largest value.

As a specific example, if the determination unit 140 determines that the output value of the auto-correlation function is "0.8", the first indicator value is 0.8 in the case of "a supine position", 0.2 in the case of a "prone position", and 0.8 in the case of "a lateral position".

(2) Calculation of Second Indicator (Step S208)

The determination unit 140 calculates a second indicator value calculated from the correlation between the waveforms of the sensors. First, with the method described above, the determination unit 140 calculates an output value of two sets of waveform data using a cross-correlation function.

Then, the determination unit 140 calculates the second indicator value by weighting the above output value. Here, a weighting method executed by the determination unit 140 is described.

With reference to FIG. 13, for example, the correlation between the waveforms of the sensors is "YES" when the posture of the user is "a supine position", "YES" or "NO" when the posture of the user is "a prone position", and "NO" when the posture of the user is "a lateral position".

The determination unit 140 executes the cross-correlation function to output any of values between "0 and 1". Here, when the correlation between the waveforms of the sensors is "YES" ("a supine position") in FIG. 13, the determination unit 140 sets the output value as the second indicator value as it is. Meanwhile, when the correlation between the waveforms of the sensors is "NO" ("a lateral position") in FIG. 13, the determination unit 140 sets, as the second indicator value, a value obtained by subtracting the output value from the largest value. Meanwhile, when the correlation between the waveforms of the sensors is "YES" or "NO" ("a prone position") in FIG. 13, the determination unit 140 sets the half of the output value as the second indicator value.

As a specific example, if the determination unit 140 determines that the output value of the cross-correlation function is "0.9", the second indicator value is 0.9 in the case of "a supine position", 0.45 in the case of "a prone position", and 0.1 in the case of "a lateral position".

(3) Calculation of Third Indicator (Step S210)

The determination unit 140 calculates a third indicator value based on the waveform output from the second calculation unit 130. For example, the determination unit 140 determines, by way of the third calculation unit 135, whether or not the ratio of the power spectrum density of the frequency of the heart beat component and integral multiplication of that frequency in the high-frequency component higher than the frequency of the breathing component is equal to or larger than a certain value. If the above ratio is equal to or larger than the certain value, the determination unit 140 determines that the waveform of heart beats is strongly superimposed on the waveform that is output from the second calculation unit 130 (i.e. the waveform output from the second calculation unit 130 largely contains the waveform of the heart beat component).

Then, the determination unit 140 outputs a value of "1" if the waveform of heart beats is superimposed on the waveform output from the second calculation unit 130, and outputs a value of "0" if the waveform of heart beats is not superimposed on the waveform output from the second calculation unit 130 (i.e. the waveform output from the second calculation unit 130 does not largely contain the waveform of the heart beat component). Further, the determination unit 140 outputs a value, obtained by weighting the output value, as the third indicator value. A weighting method executed by the determination unit 140 is described.

A description is given with reference to the chart of FIG. 13, for example. When the posture of the user is "a supine position", the waveform of heart beats is superimposed on the waveform output from the second calculation unit 130 by a small amount (i.e. the waveform output from the second calculation unit 130 contains a relatively small amount of the heart beat component). Meanwhile, when the posture of the user is "a prone position", the waveform of heart beats is superimposed on the waveform output from the second calculation unit 130 by a small amount. Meanwhile, when the posture of the user is "a lateral position", the waveform of heart beats is superimposed on the waveform output from the second calculation unit 130 by a large amount (i.e. the waveform output from the second calculation unit 130 contains a relatively large amount of the heart beat component).

Besides, in the case where the posture of the user is "a lateral position", the waveform of heart beats is superimposed on the waveform output from the second calculation unit 130 by a particularly large amount when the posture of the user is "a left lateral position".

On the other hand, when the posture of the user is "a right lateral position", the waveform of heart beats is superimposed on the waveform output from the second calculation unit 130 by a larger amount than when the posture of the user is "a supine position" or "a prone position"; however, when the posture of the user is "a right lateral position", the waveform of heart beats is superimposed on the waveform output from the second calculation unit 130 by a smaller amount than when the posture of the user is "a left lateral position".

Accordingly, when the posture of the user is "a lateral position", the determination unit 140 outputs the output value as the third indicator value as it is. On the other hand, when the posture of the user is "a supine position" or "a prone position", the determination unit 140 outputs the reduced output value (e.g. "0.1" times as large as the original output value or a value of "0") as the third indicator value.

(4) Calculation of Fourth Indicator (Step S212)

The determination unit 140 calculates a fourth indicator related to the shapes of peaks and valleys in the waveform of heart beats. In the waveform, a portion changing from valley to peak is a portion ranging from time t1 to t2 in FIG. 14 for example, and a portion changing from peak to valley is a portion ranging from time t2 to t3 in FIG. 14 for example. These portions where the waveform changes indicate the transition of vibrations (the transition of pressure), and normally correspond to the inhalation/exhalation of the user.

The determination unit 140 evaluates, for every breathing cycle (from valley to valley, or from peak to peak), how much a first time period, in which the waveform changes from valley to peak, and a second time period, in which the waveform changes from peak to valley, match between the two sensors (the vibration sensors 320a and 320b). The determination unit 140 evaluates that the vibrations sensors 320a and 320b match each other (i.e. generate a pair of outputs of the same value) if the ratio of the first time period in one cycle of the vibration sensor 320a and the ratio of the first time period in one cycle of the vibration sensor 320b fall within a predetermined range.

The determination unit 140 calculates the fourth indicator value based on the ratio by which the two sensors (the vibration sensors 320a and 320b) generate pairs of outputs of the same value in the cycles included in the posture determination section. The determination unit 140 evaluates that the two sensors (the vibration sensors 320a and 320b) match each other if, in the cycles included in the posture determination section, the number of cycles in which the sensors generate a pair of outputs of the same value exceeds a predetermined threshold.

With reference to FIG. 13, when the posture of the user is "a supine position", the waveforms of the two sensors vary in the same way. Meanwhile, when the posture of the user is "a prone position", the waveforms of the two sensors vary in the same way. Accordingly, the determination unit 140 outputs the ratio, by which the two sensors generate pairs of outputs of the same correspondence relationship with respect to time in the posture determination section, as the fourth indicator value as it is. Meanwhile, when the posture of the user is "a lateral position", the waveforms of the two sensors sometimes vary in the same way and sometimes vary in the opposite way. Thus, the determination unit 140 outputs a value obtained by multiplying the ratio, by which the sensors generate pairs of outputs of the same value in the posture determination section, by "0.5" as the fourth indicator value.

(5) Calculation of Fifth Indicator (Step S214)

The determination unit 140 calculates, as a fifth indicator, a result of comparison between the first time period in which the waveform changes from valley to peak and the second time period in which the waveform changes from peak to valley.

In this event, for every breathing cycle (from valley to valley, or from peak to peak) included in the posture determination section, the determination unit 140 compares the length of the first time period in which the waveform changes from valley to peak with the length of the second time period in which the waveform changes from peak to valley, and determines a portion where the length of the first time period is "short" and the length of the second time period is "long" ("short→long"). Then, the determination unit 140 calculates the fifth indicator value based on the ratio by which the two sensors (the vibration sensors 320a and 320b) generate pairs of outputs of time lengths both satisfying the relationship of "short→long" in the posture determination section.

For example, the determination unit 140 counts "the number of breathing cycles with the first time period shorter than the second time period" included in the posture determination section and outputs the matching ratio as the fifth indicator value.

With reference to FIG. 13, many portions satisfying the relationship of "short→long" are found in waveforms when the posture of the user is "a supine position". Thus, the determination unit 140 outputs, as the fifth indicator value, a value obtained by subtracting a value of "0.5" from the ratio by which the two sensors generate the above pairs of outputs in the posture determination section. Meanwhile, characteristics are hard to find in waveforms when the posture of the user is "a prone position" and the posture of the user is "a lateral position", and therefore the determination unit 140 does not output the fifth indicator value in those cases. In other words, the determination unit 140 outputs a value of "0" as the fifth indicator value.

In this manner, this embodiment makes it possible to determine the posture of the user using these indicator values and thereby enables the determination unit 140 to determine the posture of the user more appropriately.

Note that, in this embodiment, the determination unit 140 also determines the posture using the waveform calculated by the second calculation unit 130 based on the vibration data; however, the determination unit 140 may determine the posture of the user simply based on the vibration data. Specifically, in the processing of FIG. 12, the determination unit 140 may move the process to Steps S202 to S206 without executing Step S204.

For example, the determination unit 140 can output the third indicator by subjecting the vibration data to frequency analysis. In addition, when outputting the fifth indicator, the determination unit 140 can determine waveform's peaks and valleys in the same manner as using a waveform as long as it can extract a (neighborhood) maximum value and a (neighborhood) minimum value of the vibration data.

3. Third Embodiment

Next, a third embodiment is described. In this embodiment, a description is given of the case where the determination unit 140 determines the posture of the user using artificial intelligence (machine learning).

Figure 15:
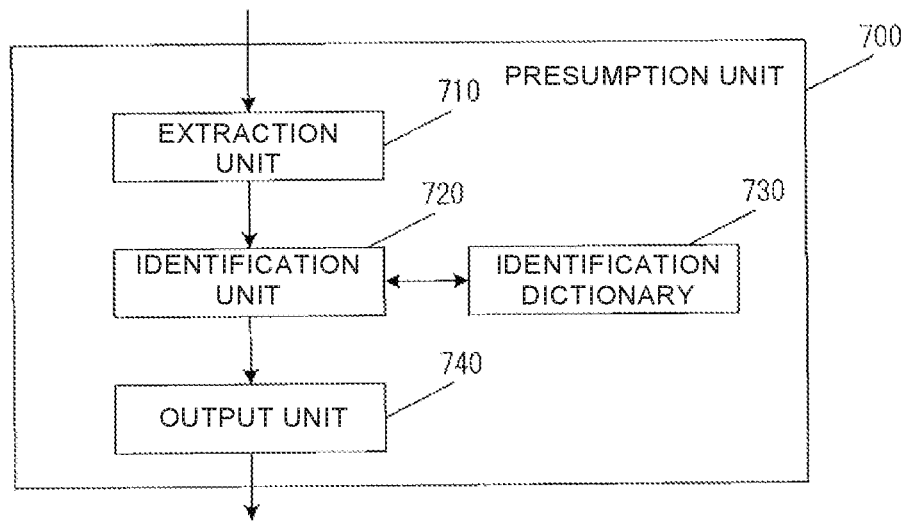
FIG. 15 is a diagram for explaining the functional configuration of a state presumption unit of a third embodiment.

In this embodiment, the posture of the user which is one factor of the state of the user is presumed based on a presumption unit 700 of FIG. 15 instead of the processing of FIG. 5.

Here, the operation of the presumption unit 700 in this embodiment is described. The presumption unit 700 presumes the posture of the user by using vibration data and the state of the user as input values (input data) and using artificial intelligence and various statistical indicators.

As illustrated in FIG. 15, the presumption unit 700 includes: an extraction unit 710; an identification unit 720; an identification dictionary 730 (learning model); and an output unit 740.

First, various parameters are input and used in the presumption unit 700. For example, in this embodiment, vibration data and waveform data calculated from the vibration data are input to the presumption unit 700.

Then, the extraction unit 710 is configured to extract various characteristic points of the input data and output them as a characteristic vector. Here, the following contents are conceivable as the contents to be extracted by the extraction unit 710 as the characteristic points.

(1) Whether or not the correlation in each sensor exists (2) Whether or not the correlation between the sensors exists (3) Whether or not the waveform of heart beats is superimposed on the waveform data (4) Whether a time period in which the waveform of breathing changes from valley to peak is shorter or longer than a time period in which the waveform of breathing changes from peak to valley (5) Whether the ratio by which a two-peak waveform appears is large or small (6) Whether or not there is a difference in area between upper and lower portions of the waveform data with respect to its center line (7) Whether or not there is a difference between the sensors in terms of the waveform of heart beats and how much the waveform of heart beats is superimposed The extraction unit 710 outputs the characteristic vector by combining one or multiple characteristic points of the above contents together. Note that the characteristic points described above are merely examples, and other contents to be extracted as the characteristic points may be combined together. In addition, values that are output by the extraction unit 710 as the characteristic points are convenient values for the sake of convenience of description. The extraction unit 710 outputs a value of "1" when the characteristic point meets the relevant condition, and outputs a value of "0" when the characteristic point does not meet the relevant condition. Note that the extraction unit 710 may output random variables as such values of the characteristic points.

If the input data contains all the characteristic points described above, a characteristic space is 7-dimensional, and the extraction unit 710 outputs them to the identification unit 720 as a 7-dimensional characteristic vector.

The identification unit 720 is configured to identify a class, which corresponds to the state of the user, based on the input characteristic vector. In this event, the identification unit 720 identifies a class by checking the input characteristic vector against multiple prototypes that are prepared in advance as the identification dictionary 730. As the prototypes, characteristic vector(s) corresponding to each class may be stored, or characteristic vectors representative of the respective classes may be stored.

When the characteristic vectors representative of the respective classes are stored in the identification dictionary 730, the identification unit 720 determines the class to which the prototype closest to the input characteristic vector belongs. In this event, the identification unit 720 may determine a class by the nearest neighbor determination rule, or may identify and determine a class by the k neighborhood method.

Note that, in the identification dictionary 730 used by the identification unit 720, prototypes may be stored in advance, or may be newly stored using machine learning and updated as needed.

Then, the output unit 740 outputs, as one factor of the state of the user, a (sleeping) posture corresponding to the class identified by the identification unit 720. As the state of the user output by the output unit 740, the output unit may identify and output "a supine position", "a prone position", or "a lateral position", or alternatively may directly output a random variable.

Thereby, according to this embodiment, the determination unit 140 can acquire vibration data output from the sensors and presume the posture of the user from the acquired information using machine learning.

4. Fourth Embodiment

A fourth embodiment is described. The fourth embodiment is an embodiment employed when the presumption unit 700 of the third embodiment presumes the posture of the user by using deep learning using neural network.

Figure 16:
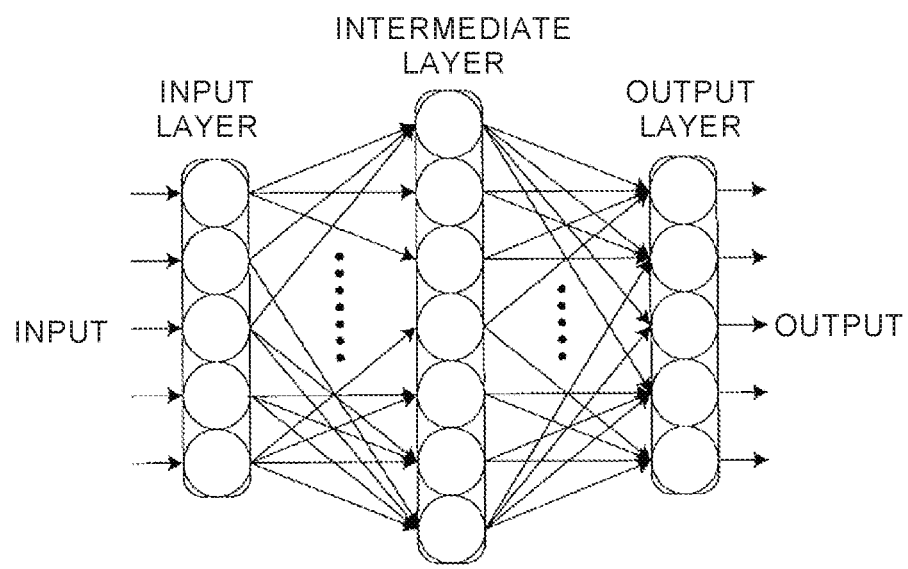
FIG. 16 is a diagram for explaining a neural network of a fourth embodiment.

In this embodiment, waveform data of the user is input to the presumption unit 700. The presumption unit 700 presumes the state (posture) of the user based on the input waveform data. The presumption unit 700 carries out estimation processing using deep learning. Note that the processing using deep learning (deep neural network) enables precise estimation particularly in terms of image recognition. FIG. 16 is a diagram for the presumption unit 700 to explain the estimation processing using deep learning.

First, the presumption unit 700 inputs a waveform data (image data) signal, output from the second calculation unit 130, to a neural network constituted of multiple layers and neurons included in each layer. Each neuron receives signals from other multiple neurons, and outputs the signals subjected to arithmetic operation to other multiple neurons. In the case where the neural network is of multi-layer structure, the layers are referred to as an input layer, an intermediate layer (hidden layer), and an output layer in the order of signal flow.

A neural network having an intermediate layer constituted of multiple layers is referred to as a deep neural network (such as Convolutional Neural Network equipped with the convolutional operation), and a machine learning method using this network is referred to as deep learning.

The waveform data flows through the neural network while changing its shape through various arithmetic operations (such as the convolutional operation, the pooling operation, the normalization operation, and the matrix operation) performed on the neurons of each layer, and multiple signals are output from the output layer.

Multiple output values from the neural network are each associated with the posture of the user. The presumption unit 700 presumes that the posture of the user is equal to the posture of the user which is associated with the largest output value. Meanwhile, the presumption unit 700 does not necessarily have to directly output the posture which is the state of the user, and may presume the posture of the user by causing one or multiple output values to pass through a classifier and presuming the posture of the user based on output(s) from the classifier.

Many sets of waveform data and the posture of the user corresponding to each set of waveform data are input to the neural network in advance as parameters which are coefficients used for the various arithmetic operations of the neural network. In addition, an error between the output value from the neural network and the correct answer value is propagated through the neural network in the reverse direction by the error back-propagation method. Thereby, the parameters of the neurons of each layer are updated plenty of times and determined. The process of updating and determining the parameters in this manner is referred to as learning.

The neural network structure and each of these arithmetic operations are explained in books and theses as publicly known techniques, and any of such techniques may be used.

In this way, the posture of the user is output by using the presumption unit 700 and with reference to vibration wave data (waveform data) calculated from the vibration data output from the sensors.

Note that, in this embodiment, the description has been given of the example where the presumption unit 700 presumes the posture of the user by using the neural network for the waveform image data. As another example, the presumption unit 700 may presume the posture of the user by simply inputting and learning vibration data (time-series voltage output values). Alternatively, the presumption unit 700 may presume the posture of the user by inputting and learning data converted into a frequency area signal through the Fourier transform or the discrete cosine transform.

5. Application Example

The following application example of the posture determination apparatus described above is conceivable by mounting it in another equipment.

[5.1 Bed]

Figure 17:
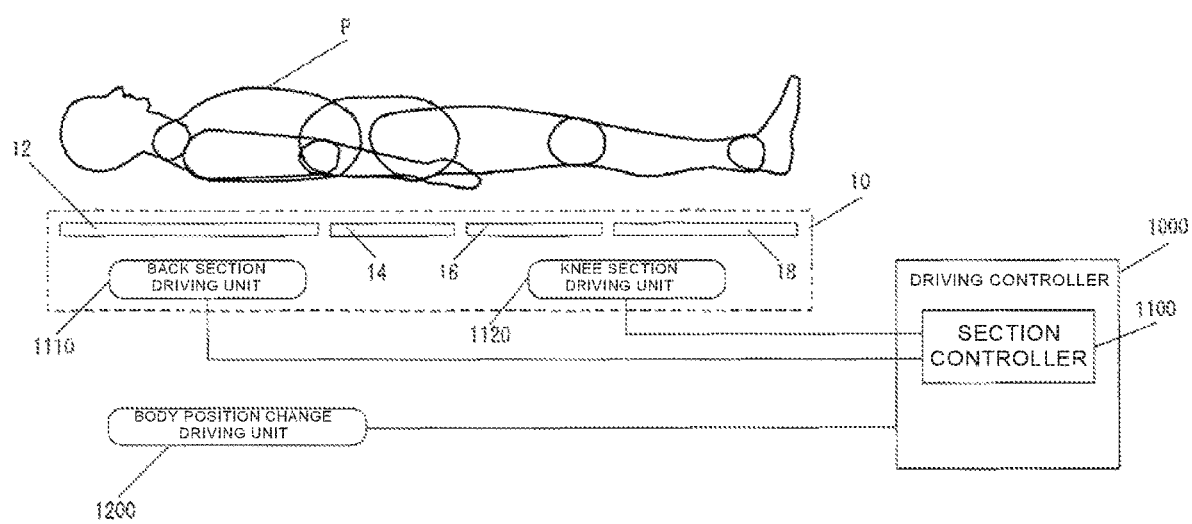
FIG. 17 is a diagram for explaining a bed as an application example.

FIG. 17 illustrates the configuration of a bed. A bed 10 includes: a back section 12; a waist section 14; a knee section 16; and a leg section 18. An upper body of a user P is supported by the back section 12 and his/her waist part is supported by the waist section 14.

A driving controller 1000 is configured to control the driving of the bed. Here, the driving controller 1000 includes the function of a section controller 1100 configured to control aback raising function, a knee raising (leg raising) function, and the like by operating the sections.

In order to implement the back raising function, the section controller 1100 is connected to a back section driving unit 1110 and a knee section driving unit 1120. The back section driving unit 1110 is an actuator, for example, and is coupled to a back raising link through a link mechanism. The back section driving unit 1110 is configured to control the operation of the placed back section 12 through the link. The back section driving unit 1110 performs back raising/back lowering control.

Meanwhile, the knee section driving unit 1120 is an actuator, for example. The knee section driving unit 1120 is coupled to a knee raising link through a link mechanism. The knee section driving unit 1120 is configured to control the operation of the knee section 16 and the leg section 18 coupled to the knee section which are placed on the knee raising link. The knee section driving unit 112 performs knee raising/knee lowering (leg lowering/leg raising) control.

In the case of the back raising operation of the bed, the section controller 1100 does not perform the back raising operation if the determination unit 140 (or the presumption unit 700) determines that the posture of the user is "a prone position". In other words, even if the user selects the back raising operation, the section controller 1100 does not drive the back section driving unit 1110 and does not perform the back raising operation. In addition, when the bed is in automatic operation, the section controller 1100 also does not perform the back raising operation if the determination unit 140 (or the presumption unit 700) determines that the posture of the user is "a prone position".

The operation in this case is described with reference to FIG. 18. First, the controller 100 determines whether or not the operation has been selected by the user (Step S302). For example, the user selects a back raising button through an input unit 160 (manipulation remote controller). Thereby, the controller 100 determines that the back raising operation has been selected.

Subsequently, the controller 100 (determination unit 140) executes the posture determination processing (Step S304). The determination unit 140 executes any of the posture determination processing described above to determine the posture of the user on the bed. Alternatively, the presumption unit 700 may determine the posture of the user in the posture determination processing.

Here, the controller 100 determines whether or not the posture of the user is a specific posture (Step S306). In this application example, the controller 100 does not execute the back raising operation if the posture of the user is "a prone position" (Step S306: Yes). If the posture is other than this posture, the controller 100 instructs the section controller 1100 (back section driving unit 1110) to execute the back raising operation (Step S306: No→Step S308).

Then, when the back raising operation is finished by the user (e.g. a stop operation is made or the back raising button is released by the user), the controller 100 stops the back raising operation (Step S310: Yes→Step S312).

In addition, the controller 100 also stops the back raising operation if the posture of the user turns to the specific posture during the back raising operation (e.g. when the posture turns to a prone position during the back raising operation) (Step S306: Yes→Step S312).

[5.2 Body Position Changing Apparatus]

The posture determination apparatus is employed in a body position changing apparatus that changes the body position of the user. For example, the controller 100 automatically stores the frequency of body position change (posture change) and the ratio of each posture for the purpose of knowing the risk of bed sores. In other words, the controller 100 automatically stores the posture of the user, determined by the determination unit 140, so that it can use these information for nursing care and treatment.

In addition, the body position changing apparatus gives notice or changes the body position automatically when the posture of the user determined by the determination unit 140 is kept the same for over a predetermined time period. For example, as illustrated in FIG. 17, the controller 100 and the driving controller 1000 control a body position change driving unit 1200. The body position change driving unit 1200 is configured to change the body position of the user by inflating and deflating air cells provided on the right and left of the user or by raising and lowering right and left sections, for example.

The driving controller 1000 controls the body position change driving unit 1200 to perform control of changing the body position of the user P according to the posture determined by the determination unit 140.

Figure 18:
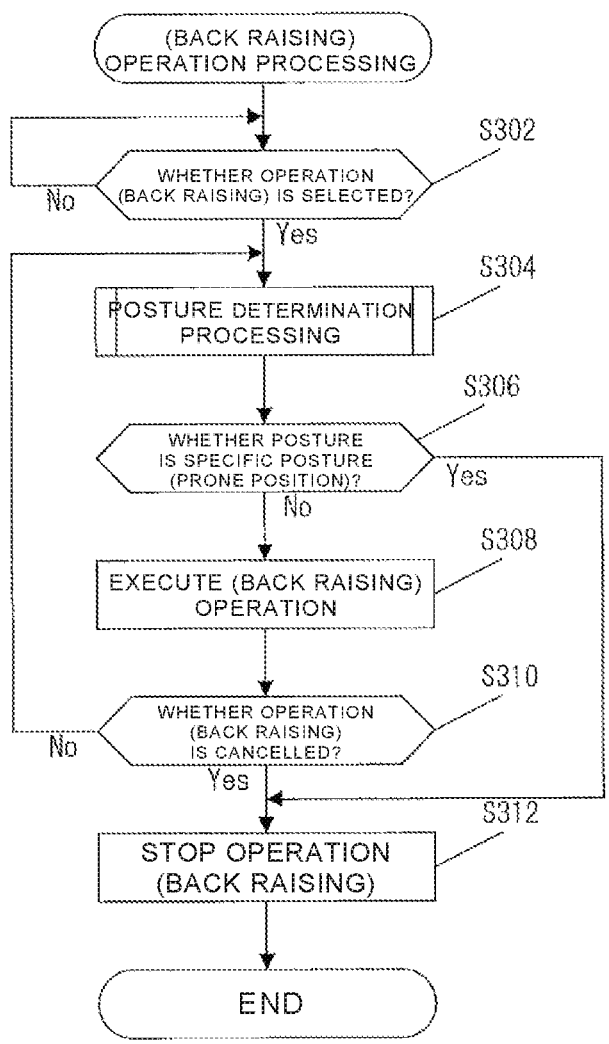
FIG. 18 is a chart for explaining processing in the case of the application example.

For example, a description is given while taking the processing in FIG. 18 as an example. Once a body position change operation is selected by the user (Step S302: Yes), the determination unit 140 determines the posture of the user by any of the methods described above (Step S304).

Here, the body position change driving unit 1200 executes the processing according to the posture determined by the determination unit 140. For example, if the user is in the posture of a right lateral position, the body position change driving unit 1200 controls the air cell provided on the right side so that the user can change his/her body position. Meanwhile, if the user is in the posture of a left lateral position, the body position change driving unit 1200 controls the air cell provided on the left side so that the user can change his/her body position. Meanwhile, if the user is in a prone position, the body position change driving unit 1200 does not control any of the right and left air cells so that the user does not change his/her body position.

The determination unit 140 may cause the body position change driving unit 1200 to change the body position of the user if determining that his/her posture is kept the same for a predetermined period. For example, the body position change driving unit 1200 changes the body position of the user if his/her posture determined by the determination unit 140 is kept the same for 10 minutes or longer.

Alternatively, the determination unit 140 may determine a change in vibration wave data (waveform data) and cause the body position change driving unit 1200 to change the body position of the user. Specifically, the determination unit 140 determines that there is a change in the posture of the user if there is a change in vibration wave data (waveform data), and changes the body position of the user if there is a change in the posture of the user. Thereby, such body position change can be used effectively for preventing bed sores on the side of the body of the user with no paralysis.

[5.3 Notification Device]

A notification device is configured to give notice according to the posture of the user determined by the determination unit 140. As a notification method of the notification device, the notification device may give notice through audio output by an audio output device or through display (light) output by a display device. In addition, the notification device may give notice to another terminal device (such as a mobile terminal device owned by a medical service worker).

The following timings are conceivable as the timing when the notification device gives notice. For example, if there is paralysis in the user, the risk of bed sores increases if the user lies with the paralyzed side down. Thus, the notification device gives notice if the posture determined by the determination unit 140 is a lateral position with the paralyzed side down.

Besides, the risk of death from suffocation increases if a baby lies with his/her face down. Thus, the notification gives notice if the posture of the user (baby) determined by the determination unit 140 is a prone position for the purpose of preventing death from suffocation.

6. Modification Example

Hereinabove, the embodiments of this invention have been described in detail with reference to the drawings; however, the specific configuration is not limited to these embodiments, and designs and the like within a range not deviating from the gist of this invention are also included in the scope of claims.

In addition, in the embodiments, the posture of the user is determined by the processing device 5 based on the result output from the detection device 3, but this determination may be made in one device. Besides, instead of implementing the processing by installing an application in a terminal device (such as a smartphone, a tablet, and a computer), the processing may be made in such a way that a server executes processing and returns a processing result to a terminal device, for example.

For example, the above processing may be implemented on the server side by causing the detection device 3 to upload vibration data to a server. This detection device 3 may be implemented by a device such as a smartphone embedded with an acceleration sensor and a vibration sensor.

In addition, the above embodiments have been described based on the premise of two vibration sensors, but vibration sensors may be provided more than two. Moreover, the method of determining the posture through calculation of frequency distribution in the first embodiment may be implemented with one sensor.

Further, the program operating in each device in the embodiments is a program that controls a CPU and the like (a program causing a computer to function) so that the CPU and the like can implement the functions of the above embodiments. Information handled in these devices is accumulated in a temporary storage device (such as a RAM) temporarily during processing, then stored in a storage device such as various ROMs, HDDs, and SSDs, and then read, modified, and written by the CPU as needed.

Furthermore, in the case of distributing the program to the market, the program can be distributed by storing the program in a portable recording medium, or can be transferred to a server computer connected via a network such as the Internet. In this case, the present invention naturally includes a storage device of a server computer.

REFERENCE SIGNS LIST

1: system, 3: detection device, 5: processing device, 10: bed, 12: back section; 14: waist section, 16: knee section, 18: leg section, 20: mattress, 100: controller, 110: detection unit, 120: first calculation unit, 130: second calculation unit, 135: third calculation unit, 140: determination unit, 150: memory, 152: vibration data storage area, 154: waveform data storage area, 160: input unit, 170: output unit, 700: presumption unit, 710: characteristic extraction unit, 720: identification unit, 730: identification dictionary, 740: output unit.

The invention claimed is:

1. A determination apparatus comprising:
at least two sensors capable of detecting a biological information when a user is lying on a bed; and
a controller configured to determine a posture of the user while the user is lying on the bed based on characteristics of the biological information,
wherein
the sensors include a first sensor and a second sensor, and the controller determines the posture of the user when the user is lying on the bed based on a correlation in a first waveform of the biological information acquired by the first sensor and a correlation between the first waveform and a second waveform, the second waveform being a waveform of the biological information detected by the second sensor.

2. The determination apparatus according to claim 1, wherein
the controller determines the posture of the user is a lateral position if the controller determines there is no correlation between the first and second waveforms and the controller determines the posture of the user is a supine position or a prone position if the controller determines there is a correlation between the first and second waveforms.

3. The determination apparatus according to claim 2, wherein
the controller determines the posture of the user is a supine position if the controller determines there is a correlation in the first waveform and the controller determines the posture of the user is a prone position if the controller determines there is no correlation in the first waveform.

4. The determination apparatus according to claim 1, wherein
the controller determines the posture of the user is a supine position if the controller determines there is a correlation in the first waveform and the controller determines the posture of the user is a prone position if the controller determines there is no correlation in the first waveform.

5. The determination apparatus according to claim 1, wherein
the controller calculates frequency distribution of the waveforms of the biological information detected by the sensors, and determines the posture of the user when the user is lying on the bed based on the frequency distribution.

6. The determination apparatus according to claim 1, wherein
the controller calculates frequency distribution of the waveforms of the biological information detected by the sensors, and determines the posture of the user when the user is lying on the bed based on the frequency distribution.

7. The determination apparatus according to claim 1, wherein
the controller determines the posture of the user based on whether or not the first and second waveforms largely includes waveforms of a heart beat component.

8. The determination apparatus according to claim 7, wherein
the controller determines the posture of the user based on how much a first time period and a second time period match between the two sensors, a waveform of the heart beat component being configured to change from valley to peak in the first time period, the waveform of the heart beat component being configured to change from peak to valley in the second time period.

9. The determination apparatus according to claim 8, wherein
the controller determines the posture of the user based on whether or not a ratio which the first time period is shorter than the second time period exceeds a threshold.

10. A bed system comprising:
a bed including a frame, a section provided on the frame, and a driver configured to drive the section;
at least two sensors capable of detecting a biological information when a user is lying on a bed; and
a controller configured to determine a posture of the user while the user is lying on the bed based on characteristics of the biological information, the controller being configured to control not to drive the section if the posture of the user is a prone position,
wherein
the sensors includes a first sensor and a second sensor, and
the controller determines the posture of the user when the user is lying on the bed based on a correlation in a first waveform of the biological information acquired by the first sensor and a correlation between the first waveform and a second waveform, the second waveform being a waveform of the biological information detected by the second sensor.

11. The bed system according to claim 10, wherein
the section can support a back of the user,
the controller is configured to control not to drive the section if the posture of the user is a prone position, even if the controller receives an instruction from the user, the instruction being a back raising command.

12. The bed system according to claim 11, wherein
the controller is configured to control to drive the section if the posture of the user is not a prone position.

13. The bed system according to claim 10, wherein
the controller determines the posture of the user is a lateral position if the controller determines there is no correlation between the first and second waveforms and the controller determines the posture of the user is a supine position or a prone position if the controller determines there is a correlation between the first and second waveforms.

14. The bed system according to claim 13, wherein
the controller determines the posture of the user is a supine position if the controller determines there is a correlation in the first waveform and the controller determines the posture of the user is a prone position if the controller determines there is no correlation in the first waveform.

15. The bed system according to claim 10, wherein
the controller determines the posture of the user is a supine position if the controller determines there is a correlation in the first waveform and the controller determines the posture of the user is a prone position if the controller determines there is no correlation in the first waveform.

16. The bed system according to claim 10, wherein
the controller calculates frequency distribution of the waveforms of the biological information detected by the sensors, and determines the posture of the user when the user is lying on the bed based on the frequency distribution.

17. The bed system according to claim 10, wherein
the controller determines the posture of the user based on at least one of (1) whether or not the first and second waveforms largely includes waveforms of a heart beat component, (2) how much a first time period and a second time period match between the two sensors, a waveform of the heart beat component being configured to change from valley to peak in the first time period, the waveform of the heart beat component being configured to change from peak to valley in the second time period, (3) whether or not a ratio which the first time period is shorter than the second time period exceeds a threshold.

* * * * *